United States Patent

Rice-Jones et al.

(10) Patent No.: US 9,173,561 B2
(45) Date of Patent: Nov. 3, 2015

(54) ALIGNMENT APPARATUS

(75) Inventors: Jennifer Margaret Rice-Jones, Faikirk (GB); Michael James Bartelme, Fort Collins, CO (US)

(73) Assignee: Optos plc (Murgitroyd), Glasgow (GB)

( * ) Notice: Subject to any disclaimer, the term of this patent is extended or adjusted under 35 U.S.C. 154(b) by 591 days.

(21) Appl. No.: 13/552,354

(22) Filed: Jul. 18, 2012

(65) Prior Publication Data

US 2014/0022270 A1 Jan. 23, 2014

(51) Int. Cl.
| | |
|---|---|
| A61B 3/10 | (2006.01) |
| A61B 3/00 | (2006.01) |
| A61B 3/14 | (2006.01) |
| A61B 3/02 | (2006.01) |
| A61B 3/12 | (2006.01) |
| A61B 3/113 | (2006.01) |

(52) U.S. Cl.
CPC .. *A61B 3/12* (2013.01); *A61B 3/113* (2013.01)

(58) Field of Classification Search
CPC .......... A61B 3/103; A61B 3/14; A61B 3/152; A61B 3/113; A61B 3/1225; A61B 3/024; A61B 3/1015
USPC ......... 351/205, 200, 206, 208–211, 221–222, 351/246
See application file for complete search history.

(56) References Cited

U.S. PATENT DOCUMENTS

| | | | |
|---|---|---|---|
| 3,864,030 A | 2/1975 | Cornsweet | |
| 5,905,562 A * | 5/1999 | Isogai et al. | 351/208 |
| 6,280,436 B1 | 8/2001 | Freeman et al. | |
| 6,712,809 B2 | 3/2004 | Li et al. | |
| 2004/0054277 A1* | 3/2004 | Uchida | 600/399 |
| 2004/0263784 A1 | 12/2004 | Cornsweet et al. | |
| 2009/0125849 A1 | 5/2009 | Bouvin et al. | |
| 2012/0242955 A1* | 9/2012 | Yoshino et al. | 351/208 |

FOREIGN PATENT DOCUMENTS

| | | |
|---|---|---|
| JP | 2000005150 A | 1/2000 |
| WO | 2004049258 A1 | 6/2004 |

OTHER PUBLICATIONS

User Guide OPTOS, 200Dx, pp. 95, Sep. 2010.
User Guide OPTOS 200Tx, pp. 105, Feb. 2011.

* cited by examiner

*Primary Examiner* — Dawayne A Pinkney
(74) *Attorney, Agent, or Firm* — Drinker Biddle & Reath LLP

(57) ABSTRACT

An alignment apparatus and method is disclosed, for ensuring correct alignment of a patient's eye with respect to an ophthalmic or optometric instrument. Graphical objects are provided which represent an ideal and an actual position of the eye, and provide for easy and intuitive feedback to an eye care professional operating the instrument on the alignment position of the patient.

30 Claims, 8 Drawing Sheets

ALIGNMENT APPARATUS

FIELD OF THE INVENTION

The present disclosure relates to an alignment apparatus and associated method, particularly but not exclusively for aligning an eye for examination by an ophthalmic or optometric instrument.

DESCRIPTION OF THE RELATED ART

Examples of ophthalmic or optometric instruments include ophthalmoscopes, scanning laser ophthalmoscopes, slit lamps, fundus cameras and so on.

Fundus cameras comprise microscopes with attached cameras for photographing the interior surface of the eye including the retina, optic disc, macula and fundus. They may use various ophthalmoscopy techniques and image processing techniques such as optical coherence tomography (OCT).

In general, it is important that a patient's eye is correctly positioned in the relevant apparatus. This is particularly important for diagnostic applications where in-focus images of the retina or other parts of the eye are required, and where incorrect positioning of the eye can cause a resulting diagnosis to be unreliable, or for features to be mis-characterized or altogether unseen by an operator of the equipment.

It is known for existing equipment to be provided with one or more cameras for capturing an exterior image of the eye, a display and image processing software so that an operator of the equipment can be provided with a live video image of the patient's eye together with an indication of the positioning of the eye. The positioning information is provided in some instances in the form of absolute positional coordinates which are presented on the display.

It is also known for alignment in an x,y plane (the plane of motion of a patient's eye left to right (x) and up and down (y)) to be monitored by lining up a limbus in a video of the eye with a fixed ellipse, which changes color when an alignment is achieved. It is also known for alignment along a z-axis (the distance between a patient's eye and the instrument) to be represented with a single graphical object, which takes the form of a "plus" or "minus" sign, indicative of the patient's eye being either too far away or too close, and then changes to a circle when a correct alignment is achieved. These alignment mechanisms can be found for example in the 200Dx and 200Tx ultrawide field retinal imaging systems available from OPTOS PLC, Queensferry House, Carnegie Campus, Enterprise Way, Dunfermline, Scotland KY11 8GR United Kingdom. However, the x and y alignment mechanism can be difficult to use, because it relies upon making an alignment of two ellipses; and the z-alignment mechanism provides only a coarse indication of the actual eye position. For all these systems, when a patient's eye is not in an ideal position, it is difficult for an operator of the equipment to ascertain quickly and intuitively which correctional motion is required in order to bring the eye into the correct position. This lack of intuition slows down the eye examination and can increase the likelihood of the operator making errors, in particular in cases where the patient's eye position moves away from an ideal position during the use of the apparatus.

It is an object of the disclosure to provide an intuitive and readily understood indication of a patient's eye position when under examination by an ophthalmic or optometric instrument.

BRIEF SUMMARY OF THE INVENTION

According to a first aspect of the disclosure there is provided an alignment apparatus comprising: an ophthalmic or optometric instrument; a camera arranged to image a patient's eye, in use; a processor arranged to receive image data from the camera and to process the image data to determine an eye position; and a display; wherein the processor is arranged to form on the display a first graphical object representative of an ideal eye position and a second graphical object representative of an actual eye position, as determined by the processor.

Optionally, the processor applies an edge detection algorithm to the image data and identifies the center point of a pupil of an eye.

Optionally, the apparatus comprises two cameras, each arranged to image a patient's eye.

Optionally, the eye position is determined in three dimensions.

Optionally, the processor is arranged to form on the display an image of a patient's eye, and the first and second graphical objects are overlaid upon the image.

Optionally, the processor is arranged to form on the display a second graphical object having a first color in the event of a determined eye position being out of alignment with respect to an ideal eye position and to form on the display a second graphical object having a second color in the event of a determined eye position being in alignment with respect to an ideal eye position.

Optionally, the first graphical object comprises a crosshair element.

Optionally, the second graphical object comprises a spot, displayed at a center point of a pupil of an eye.

Optionally, the first graphical object comprises a series of radially spaced markers.

Optionally one of the markers is graphically distinguished from the other markers and represents an ideal eye position.

Optionally, the second graphical object comprises a marker at a radial position which is overlaid upon one of the radially spaced markers of the first graphical object or formed by changing a display property of one of the radially spaced markers of the first graphical object.

Optionally, a history of an eye's motion can be displayed by displaying two or more of the second graphical objects.

Optionally, the first and second graphical objects comprise concentric ring shaped elements.

Optionally, the first graphical object comprises a first crosshair graphical element and a second graphical element comprising a series of radially spaced markers.

Optionally the second graphical element comprises a first spot graphical element and a second graphical element comprising a marker at a radial position which is overlaid upon one of the radially spaced markers of the second graphical element of the first graphical object or formed by changing a display property of one of the radially spaced markers of the second graphical element of the first graphical object.

According to a second aspect of the disclosure there is provided an alignment method comprising: positioning a patient's eye for examination by an ophthalmic or optometric instrument; imaging the eye with a camera; outputting image data from the camera to a processor; determining, at the processor, an eye position; coupling a display with the processor; and forming on the display a first graphical object representative of an ideal eye position and a second graphical object representative of an actual eye position, as determined by the processor.

Optionally, an operator performs a visual inspection of the display, and adjusts the alignment of the patient's eye with respect to the instrument based on the visual inspection.

Optionally, the processor applies an edge detection algorithm to the image data and identifies a center point of a pupil of an eye.

Optionally, the step of imaging the eye with a camera comprises imaging the eye with different first and second cameras.

Optionally, the eye position is determined in three dimensions.

Optionally, the processor forms on the display an image of a patient's eye, and overlays the first and second graphical objects upon the image of the eye.

Optionally, the processor forms on the display a second graphical object having a first color in the event of a determined eye position being out of alignment with respect to an ideal eye position and to form on the display a second graphical object having a second color in the event of a determined eye position being in alignment with respect to an ideal eye position.

Optionally, the first graphical object comprises a crosshair element.

Optionally, the second graphical object comprises a spot, displayed at a center point of a pupil of an eye.

Optionally, the first graphical object comprises a series of radially spaced markers.

Optionally one of the markers is graphically distinguished from the other markers and represents an ideal eye position.

Optionally, the second graphical object comprises a marker at a radial position which is overlaid upon one of the radially spaced markers of the first graphical object or formed by changing a display property of one of the radially spaced markers of the first graphical object.

Optionally, a history of the eye's motion is displayed by displaying two or more of the second graphical objects.

Optionally, the first and second graphical objects comprise concentric ring shaped elements.

Optionally, the first graphical object comprises a first crosshair graphical element and a second graphical element comprising a series of radially spaced markers.

Optionally the second graphical element comprises a first spot graphical element and a second graphical element comprising a marker at a radial position which is overlaid upon one of the radially spaced markers of the second graphical element of the first graphical object or formed by changing a display property of one of the radially spaced markers of the second graphical element of the first graphical object.

According to a third aspect of the disclosure there is provided a computer program product encoded with instructions that when run on a computer, cause the computer to receive image data; determine an eye position from the image data; and transmit a display signal for forming on the display a first graphical object representative of an ideal eye position and a second graphical object representative of an actual determined eye position.

The computer program product may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The instructions or code associated with a computer-readable medium of the computer program product may be executed by a computer, e.g., by one or more processors, such as one or more digital signal processors (DSPs), general purpose microprocessors, ASICs, FPGAs, or other equivalent integrated or discrete logic circuitry.

BRIEF DESCRIPTION OF THE DRAWINGS

The disclosure is described below, by way of example only, with reference to the accompanying drawings, in which.

DETAILED DESCRIPTION OF THE INVENTION

Figure 1:
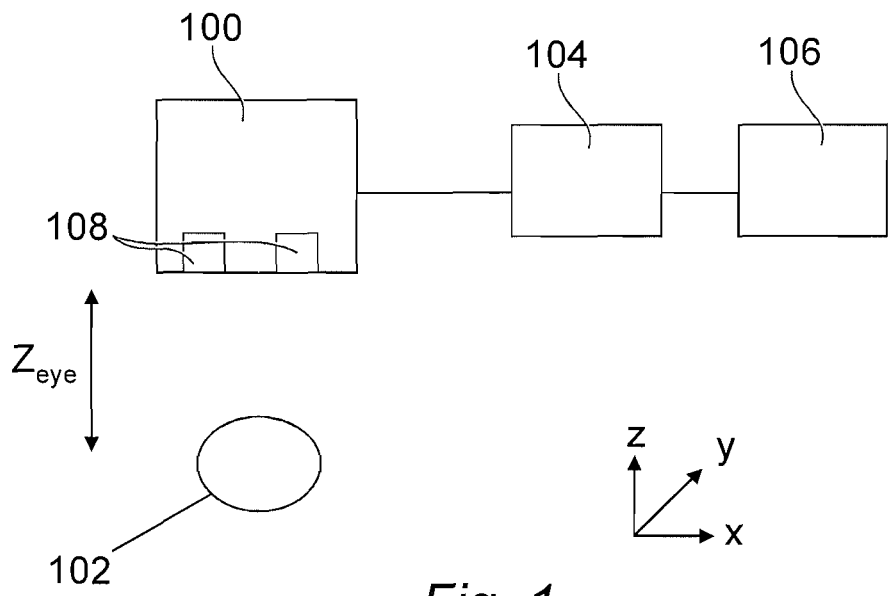
FIG. 1 illustrates aspects of an ophthalmic or optometric apparatus.

FIG. 1 illustrates an ophthalmic or optometric apparatus. An instrument 100 is provided for examination of a patient's eye 102. The instrument 100 is coupled with a processor 104, which may be an integral part of the instrument 100 or provided as (or as part of) a separate computer such as a personal computer. The processor 104 provides control signals for forming images on a display 106. Again the display 106 may be an integral part of the instrument 100 or part of a separate computer coupled with the instrument 100. The processor also receives data from the instrument 100, as described below.

The instrument 100 is used by an operator, being a different person from the person under examination and whose eye 102 is being imaged. The operator may be an eye care professional with suitable training and/or qualifications such as an ophthalmologist, orthoptist, optometrist or nurse; or a trainee or assistant under the supervision of such a person.

Various peripherals may be provided, for example, a computer keyboard and pointing device for interaction with the computer system, and/or various control mechanisms for the instrument 100. Depending on the type of instrument, these control mechanisms may be push buttons, joysticks, sliders, and touch screen controls for example. The instrument 100 also provides one or more cameras 108 for imaging the eye 102.

In the illustrated example, two cameras 108 are present. However it is possible for a different number of cameras to be provided. In particular, it is possible to perform the methods described herein using only a single camera; or alternatively multiple cameras, three or more, may be provided to provide further enhancements.

The cameras 108 have the purpose of coordinating patient alignment in accordance with the present disclosure. However it is possible in some embodiments, depending upon the type of ophthalmic or optometric instrument 100 provided, that the instrument 100 itself may have a primary camera for performing the main instrumentation function of the instrument. In that scenario it is possible for the instrument's primary camera to have a dual function and also to be used as the camera 108 for performing the methods described herein. Alternatively, even when a primary objective camera is provided, one or more further separate cameras 108 may be provided in order to perform the functions of the disclosure as described herein.

A patient's eye 102 will be positioned a distance, $z_{eye}$ from the instrument 100, along a z axis. A three-dimensional position of the eye 102 may be defined according to the x, y and z axes as shown in the Figure. In a preferred embodiment, the z-axis is also perpendicular to an image sensing plane of the camera 108. In a further preferred embodiment, the plane spanned by the x and y axes will correspond to the coronal plane of an ideally-positioned (sitting or standing perfectly straight, or lying perfectly flat) patient, namely for a sitting or standing patient the x-y plane will be a horizontal-vertical plane, while for a supine patient the x-y plane will be a horizontal plane.

Correct determination of the position of the eye (in two or three dimensions) is important for correct operation of the instrument 100. Variation of the position in any of the dimensions can cause problems. For example it may result in a poor quality image or a reduced scan field in the case of a laser scanning ophthalmoscope as a result of iris clipping.

The camera 108 may comprise an image sensor formed from an array of pixels, manufactured as charge coupled devices (CCD) or using complementary metal oxide semiconductor (CMOS) techniques. Pixels are sensitive to incident electromagnetic radiation and produce a signal intensity value after performing a charge to voltage conversion. A set (or subset) of signal intensity values across the array is referred to as "image data", with successive sets of data recovered at different times being referred to as successive "frames" of image data.

The image data is then subject to various post-processing steps in order to render an image, either for viewing by a human user or for processing by a machine. The post-processing can include various statistical analysis of the image data to perform various tasks. Examples of such tasks include edge detection and object tracking. Edge detection algorithms can identify areas of an image representing the edges of an object, based on analysis of the changes in detected intensity of the image data values. Motion detection algorithms can then be applied to examine the image data between successive frames, in order to track the position of an object.

In more detail, an example of a suitable alignment algorithm takes as its input sequential pairs of eye images from the alignment cameras. The centers of the eyes in each image will have coordinates $(x_1, y_1)$ and $(x_2, y_2)$. The algorithm operates on a single pair of images at a time, one from each camera, as follows:

1. A "Canny edge detector" (a well known technique, developed by John F. Canny of the University of California, Berkeley) detects edges in each of the two images.
2. An ellipse finder looks for ellipses in the detected edges and identifies the edges of the pupil in each image.
3. $(x_1, y_1)$ and $(x_2, y_2)$ are the coordinates of the centre of the detected pupil ellipse in each image.
4. The x coordinate of the pupil to be output, $x_p$, is calculated as the average of $x_1$ and $x_2$.
5. The y coordinate of the pupil to be output, $y_p$, is calculated as the average of $y_1$ and y2.
6. The z coordinate of the pupil to be output, $z_p$, is calculated as the difference between the two x coordinates, multiplied by a scaling factor, F. The scaling factor relates to the specific setup of the two cameras. This relies on the cameras being at the same y position. If cameras were mounted at the same x position and different y positions, then the z coordinate of the pupil to be output, $z_p$, is calculated as the difference between the two y coordinates, multiplied by a scaling factor, F.

Thus, the algorithm can output the x, y and z axes of the detected center of the pupil; and also a Boolean "locked" value indicating whether or not the algorithm detected a pupil. This is used to flag whether the x, y and z values are valid and suitable for use by the user interface.

According to a preferred embodiment the present disclosure applies edge detection to identify the outer edge of the pupil of the eye 102. A center point of the pupil is then calculated based on the detected outer pupil edge. Other image processing techniques may also be applied, such as motion tracking, and/or ellipse fitting.

In an embodiment where a single camera 108 is provided, the motion of the eye 102 in the x and y directions can be tracked. In addition, the position in a z direction can be monitored by tracking changes in size of the detected limbus. As the patient's eye moves in the z axis towards the instrument 100, the apparent size of the limbus will increase, while if the patient's eye 102 moves away from the instrument 100 in the z axis the apparent size of the limbus will decrease. The various different detected sizes can then be correlated to positions along the z axis.

In embodiment where two or more cameras are provided, their relative geographical positions will be known and so the x and y readouts of the patient's eye position can be correlated to provide an absolute x and y position of the patient's eye 102. In addition, the use of two spaced cameras provides stereopsis which can give depth information i.e. a position in the z axis.

The image processing may be carried out by image processing circuitry provided as part of the processor 104, or alternatively as part of the cameras 108.

For the purpose of imaging by the camera 108, the patient's eye 102 may also be illuminated by a light source. (In FIG. 1 the light source is provided integrally with the camera/cameras 108 although it may be provided as a separate element). One example of a suitable light source is an illuminator that emits infrared (IR) or near-infrared (NIR) radiation, such as a light emitting diode (LED) or other equivalent. The use of an IR or NIR illuminator means that the pupil of the patient's eye 102 is not constricted during use.

The processor 104 is arranged to form on a display 106 a first, or reference, graphical object representing an ideal position for a patient's eye, and a second graphical object representing the actual position of the eye as derived from the image data generated by the camera 108.

Figure 2:
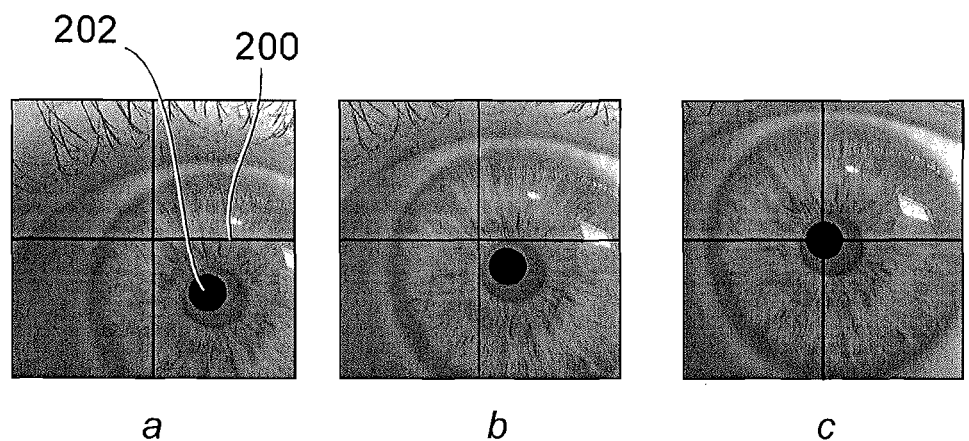
FIG. 2 illustrates a first embodiment, where alignment of a first graphical object with a second graphical object can be used to track the position of a patient's eye in an x-y plane.

FIG. 2 illustrates aspects of a first embodiment, and variations thereof. In this embodiment, the first graphical object 200 comprises a crosshair graphical element, optionally with an outer ring. According to the first embodiment the second graphical object 202 comprises a spot. This spot may be displayed at a centre point of a detected pupilas detected by the image processing carried out by the processor 104, thus corresponding to the pupil position of the eye 102. The term "spot" used herein is not limited to a circular graphical object. Rather it is equivalent to a point, square, star or any other marker that can be used to indicate a specific location.

Figure 3:
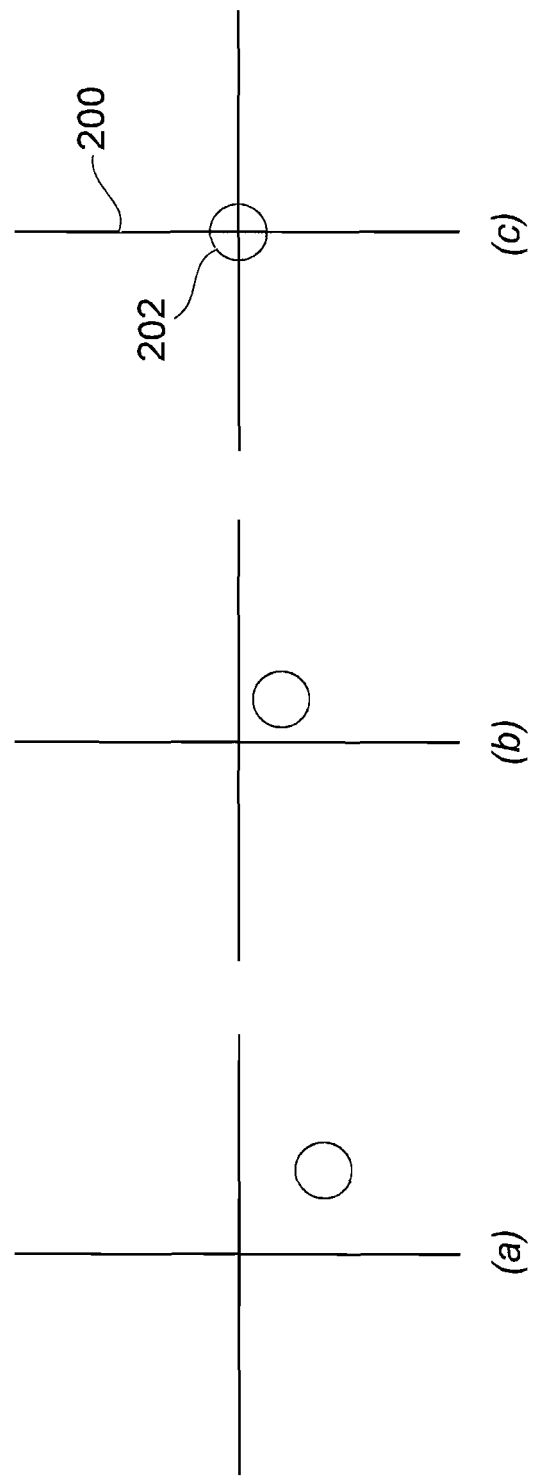
FIG. 3 illustrates aspects of the embodiment shown in FIG. 2.

FIG. 3 illustrates the same graphical objects 200, 202 of FIG. 2 without the background eye image, for clarity of illustration. The same positions are illustrated in FIGS. 2 (a), (b) and (c) as are illustrated in FIGS. 3 (a), (b) and (c) respectively.

An operator of the instrument 100 can therefore view the display 106, compare the relative positions of the first and second graphical objects 200, 202 and determine whether the patient's positioning is correct based upon that comparison. The operator can then, while maintaining their gaze on the display 106, make an adjustment to the alignment of the eye 102 with respect to the instrument 100.

The way in which the alignment adjustment is made will depend upon the type of apparatus that the instrument 100 is or forms part of, however it is in general possible for either the patient or the instrument to be moved in order to adjust the alignment, or for both the instrument and the patient to move. For example, an operator can achieve patient movement by issuing a verbal instruction for them to move their head, or by physical manipulation by the operator of the patient's head, either directly or by adjusting a patient positioning mechanism such as a chair or bed position. Or, in the case where the instrument 100 is a slit lamp, a chin rest will be provided for the positioning of the patient's head. The chin rest position and/or the lamp position can be altered using slit lamp controls, in response to the determination of the eye 102 position based upon the relative positions of the first and second graphical objects.

The operator can then know that a patient is in the correct position from a visual inspection to determine when the first and second graphical objects are aligned.

It is also possible, as an optional improvement, for a color of the second graphical object 202 to be different depending on whether or not a patient's eye 102 is correctly aligned or not. In the example embodiment shown in FIG. 2, the second graphical object 202 would be a first colour in FIGS. 2A and 2B, where there is an alignment mismatch, and a second different colour in the case of FIG. 2C where alignment occurs. Any color can be chosen however suitable colours in one embodiment would be red for a non-aligned position as in FIGS. 2A and 2B and green for an aligned position as in FIG. 2C. The first graphical object 200 may be chosen to have a colour the same as or different from one or more of the colours chosen for the different states of the second graphical object 202. In one example embodiment, the first graphical object 200 will be a different colour from either color of the two different states of the second graphical object 202, for example orange. The colour may be intentionally chosen to provide a contrast to the color or colors used for the second graphical object 202.

The change in color may occur when an alignment to within a predetermined threshold is achieved. The threshold can be chosen based on the nature of the instrument 100 and the conditions that it is being used to investigate. There may be some situations where a relatively greater alignment error can be tolerated while still yielding results that are deemed acceptable for the given application. In an optional feature of this and other embodiments, the threshold for alignment tolerance can be adjusted, preferably via a variable parameter in control software provided as part of a user interface, for defining control signals to be sent to the processor.

The embodiment illustrated in FIG. 2 is particularly suited for determining the correct position of a patient's eye 102 in the x and y planes. The position of the spot 202 in a vertical and horizontal axis of the screen of a display 106 corresponds to the position in the x and y plane of the eye 102.

Figure 4:
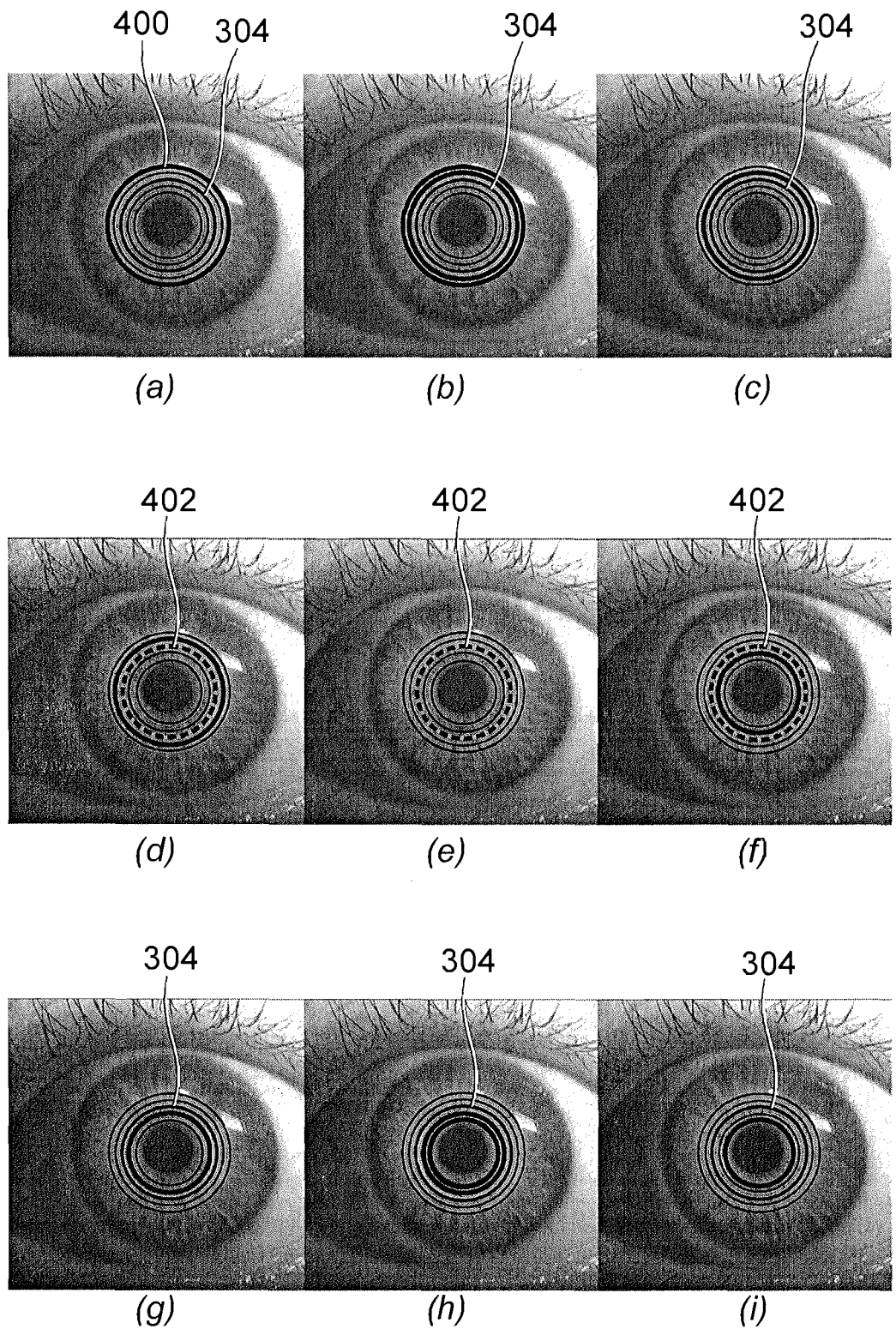
FIG. 4 illustrates a second embodiment comprising first and second graphical objects which can be compared for tracking the position of a patient's eye along a z-axis between the eye and an instrument.

FIG. 4 illustrates an alternative embodiment of the disclosure, which is particularly suited for determining the correct position of an eye 102 in the z direction as shown in FIG. 1. An example first, or reference, graphical object representing an ideal position for a patient's eye and may comprise a set of markings representing different radial positions as measured from a centre point. In a specific embodiment, the set of markings comprises a series of concentric rings.

In an optional implementation, one of the markings may be graphically distinguished from the other of the markings, and represent an ideal position. The selected marking is a specific concentric ring which is made bolder than the other concentric rings. Other methods of graphically distinguishing the ideal position marking from the other markings include for example making the ideal position marking a different color from the other markings, or providing an animation effect such as a flashing or a pulsing.

In one embodiment the ideal position marking will be in a middle section of the set of markings, namely, there will be one or more markings provided on both sides of the ideal position representing variations from the ideal position in two different directions along the z-axis.

FIG. 4 shows an example of a first graphical object 300 comprising a set of concentric rings. This is used in combination with a second graphical object, where the second graphical object represents the actual position of the eye 102 as derived from the image data generated by the camera 108. The second graphical object may also comprise a marking representing a radial position. An example of a suitable second graphical object is shown in FIG. 4. Here, a second graphical object 400 comprises a ring 400.

The ring 400 may be provided as a separate graphical object overlaid on the first graphical object 300. Alternatively, the second graphical object 400 may be provided as a modification that is selectively applied to the first graphical object 300. In the example shown, the modification may comprise changing a color or other visual property of a selected one or a plurality of the rings 302.

The second graphical object 400 represents an actual measured position of the patient's eye 102 along z axis. As described above, the z axis positional information is derived from the image data from the camera or cameras 108 and the processor 104. In one embodiment a single camera 108 can be provided and the z position can be determined by the size of the limbal ring. In an alternative embodiment the depth position can be determined through stereopsis effects where two or more cameras are provided. The relative position of the patient's eye 102 and the instrument 100 can then be adjusted until the second graphical object 400 corresponds to or overlays the ideal position marking 304 of the first graphical object. In one embodiment the distance of the eye 102 from the instrument 100 increases with the radial position of the markings 302. When an ideal position marking 304 is provided, markings that are outside (at a greater radial position with respect to) the ideal position marking 304 represent positions where the patient's eye 102 is further away from the instrument 100 than an ideal position, and markings that are inside (at a lesser radial position with respect to) the ideal position marking 304 represent positions where the patient's eye 102 is closer to the instrument 100 than an ideal position.

It is also possible, as an optional improvement, for a colour of the second graphical object 400 to be different depending on whether or not a patient's eye 102 is correctly aligned or not. As for the embodiment described with reference to FIG. 2, any colour can be chosen however suitable colours in one embodiment would be red for a non-aligned position and green for an aligned position. The first graphical object 300 may be chosen to have a color the same as or different from one or more of the colors chosen for the different states of the second graphical object 400. In one example embodiment, the first graphical object 300 will be a different colour from either color of the two different states of the second graphical object 400, for example orange. The colour may be intentionally chosen to provide a contrast to the color or colors used for the second graphical object 400.

It is also possible to display motion history of the patient's eye 102. The current position of the eye 102 can be displayed via a first portion of the second graphical object 400 while one or more previous temporal positions of the eye 102 may also be displayed via a second portion of the second graphical object 400. This gives an operator an idea of how a patient's eye 102 is moving.

In FIG. 4, diagrams 4*a* through 4*i* represent a sequence of motion where a patient's eye moves from a first extreme position too far away from the instrument 100, represented by FIG. 4*a*, through a sequence of positions to an alignment position FIG. 4*e* and on to a position where the eye 102 is too close to the instrument 100, shown in FIG. 4*i*. In FIGS. 4*d*, 4*e* and 4*f* the second graphical object comprises an indicator 402 that the eye is in an aligned position. In this embodiment the indicator is represented by a green ring. FIG. 4*e* represents the state where the eye is being held steady in a correctly aligned position, however FIG. 4*d* shows an example where the eye has just moved into the correct position from a position slightly too far away from the instrument 100, while FIG. 4*f* shows that an eye has moved away from the correct position to a position too close to the instrument 100.

An operator can therefore adjust the alignment of the patient (and thus their eye 102) with respect to the instrument 100 according to the categories explained above and based upon comparison of the alignment of the first graphical object 300 with respect to the second graphical object 400.

Figure 5:
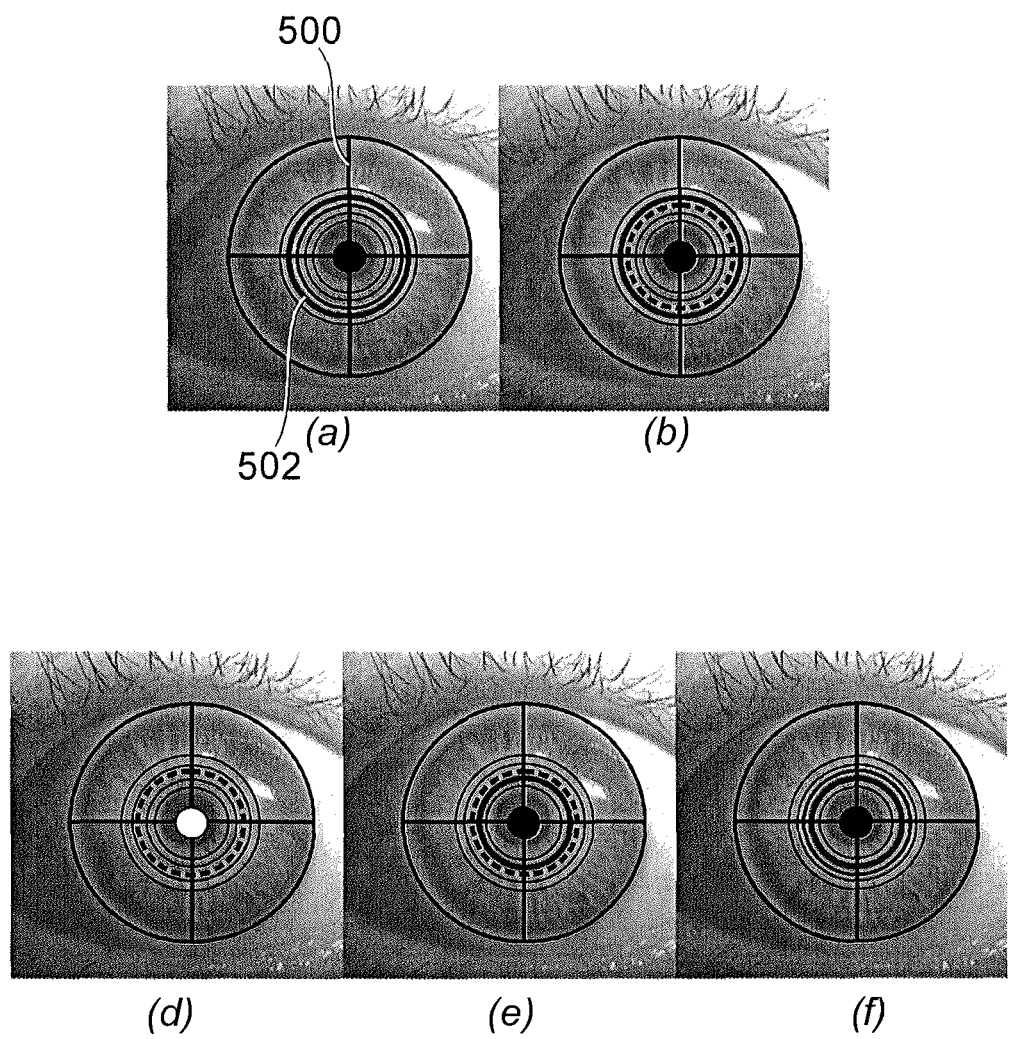
FIG. 5 illustrates a third embodiment, comprised of a combination of the graphical objects illustrated in FIGS. 2 and 3 and the graphical objects illustrated in FIG. 4. The figure shows various example views for different eye positions along a z-axis.

It is possible to combine an x and y measurement system with a z measurement system in a single graphical interface. FIG. 5 shows an example of this combination, formed from the combination of the embodiment illustrated in FIG. 2 with the embodiment illustrated in FIGS. 3 and 4.

In this example, a first graphical object 500 comprises a first element for representing an x, y plane position and a second element for representing an ideal z position. Similarly the second graphical object 502 comprises a first element for representing the measured x, y position of the eye 102 and a second element for showing the actual measured z position of the eye 102. In the embodiment illustrated, the first graphical object 500 comprises a crosshair and a series of concentric rings, each according to the embodiments mentioned above, while the second graphical object 502 comprises a spot in combination with radially spaced rings in accordance with the embodiments mentioned above.

The same features mentioned above can be used in this embodiment, so an operator knows that a patient's eye 102 is in the correct position when both elements of the second graphical object are highlighted in a specific color, for example a green color.

It is possible as an alternative to provide embodiments where the ideal position marking is the outmost or innermost ring from a set of concentric rings. In that embodiment, the other concentric rings can be used to indicate when the eye is too far away, and if the eye is too close, then the ideal position marking can change color.

Figure 6:
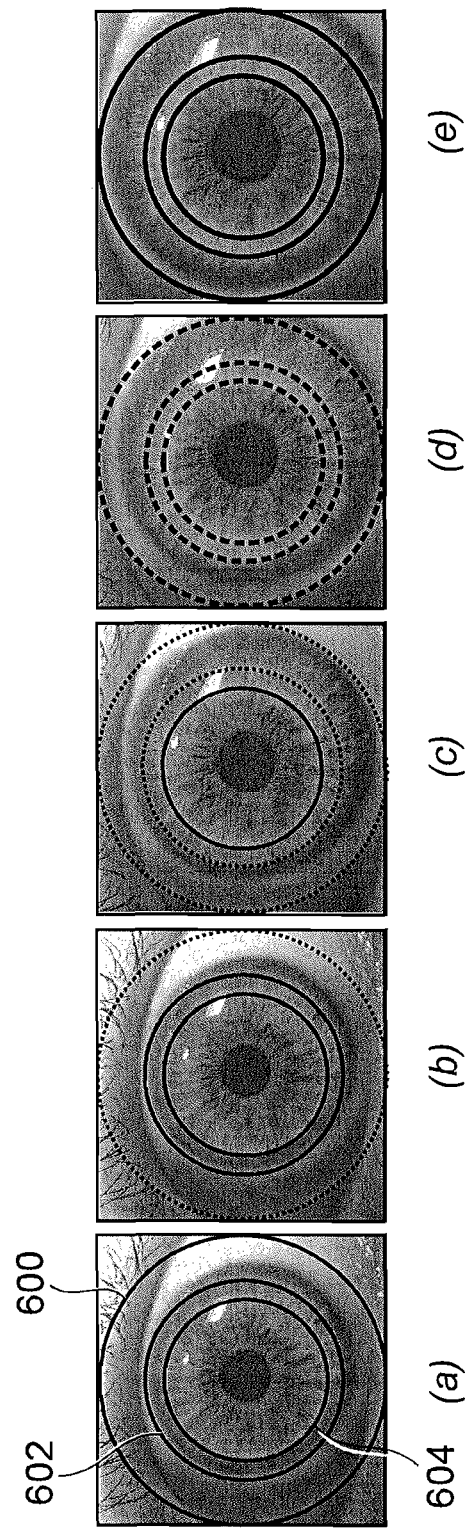
FIG. 6 illustrates a fourth embodiment, with alternative first and second graphical objects which can be compared for tracking the position of a patient's eye along a z-axis between the eye and an instrument.
Figure 7:
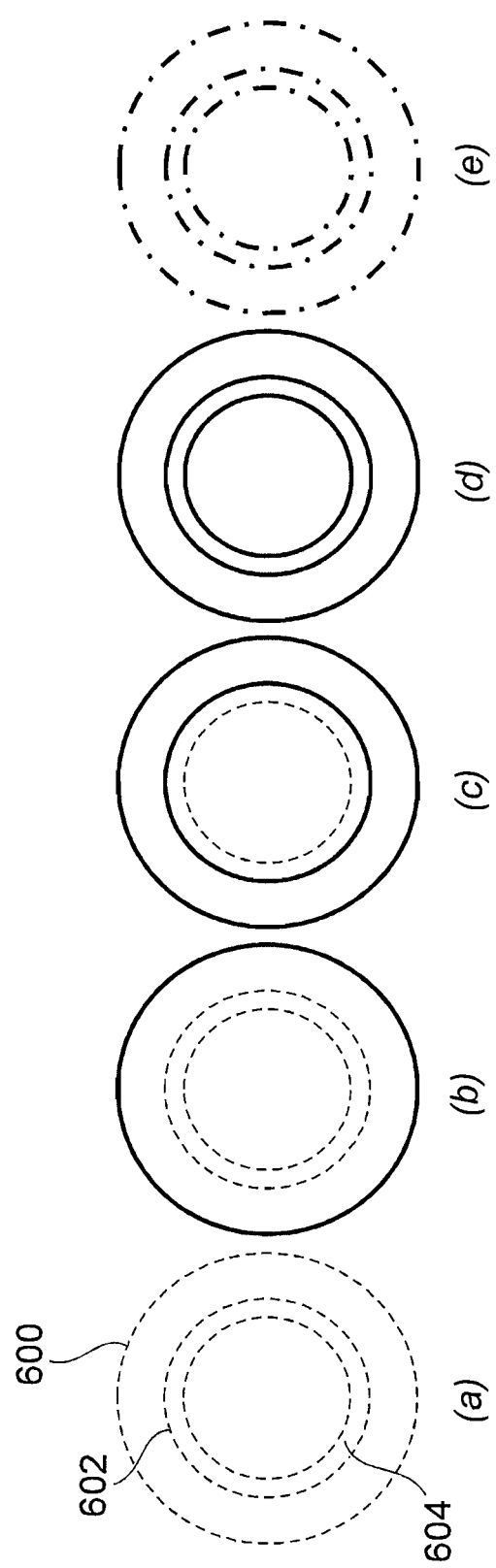
FIG. 7 illustrates aspects of the embodiment shown in FIG. 6.

An example of this embodiment is illustrated in FIG. 6, which shows the operation of a z axis alignment marker mechanism in isolation. FIG. 6(*a*) shows a position where no eye is detected and all of the rings 600, 602, 604 are of a first color. There may of course be more or fewer rings provided according to specific variations of this embodiment. FIG. 6(*b*) shows a position where the eye is much too far away, in which case the first ring 600 is displayed as a second color different from the first color. FIG. 6(*c*) shows a position where the eye is still too far away and in which case the first and second rings 600, 602 are of the second color while the central ring 604 remains of the first color. FIG. 6(*d*) shows an embodiment where the eye position is just right, in which case all of the rings 600, 602, 604 are of a third color which in one embodiment may be green, indicating a correct z position of the eye. If the eye is moved too close to the instrument, all of the rings then turn to a fourth color which in a preferred embodiment is red, as shown in FIG. 6(*e*). FIG. 7 illustrates the same embodiment shown in FIG. 6 with the background eye image removed for clarity of illustration.

Figure 8:
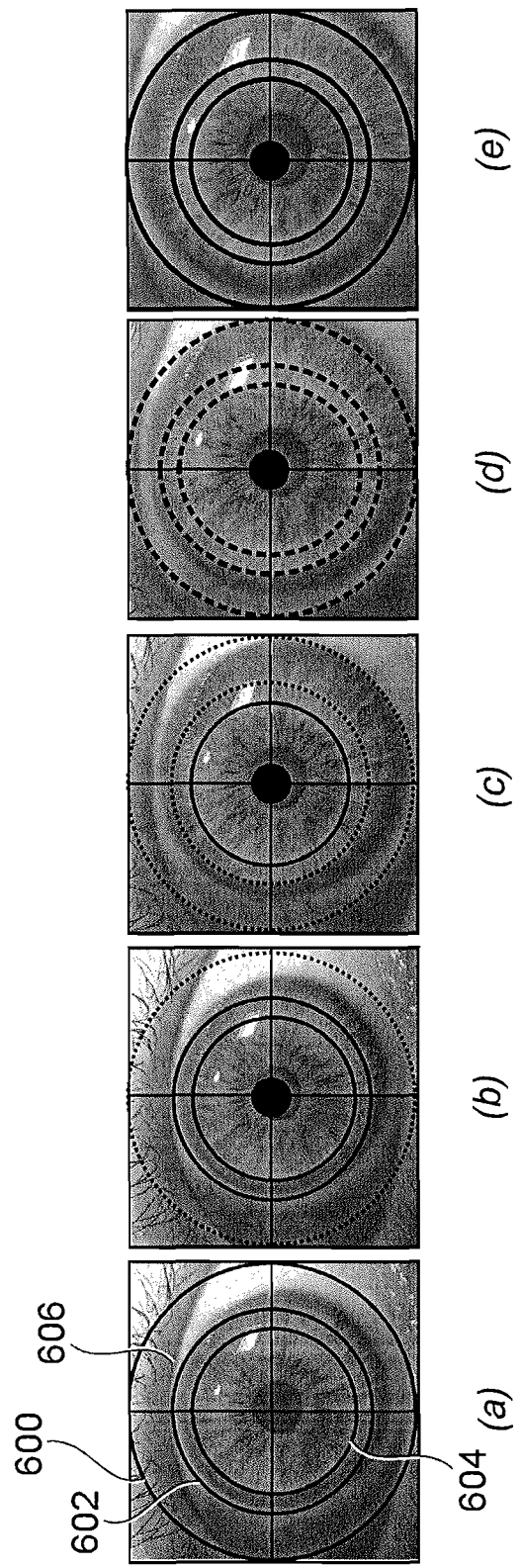
FIG. 8 illustrates the embodiment of FIG. 6, in combination with an x,y alignment mechanism.

FIG. 8 illustrates the embodiment shown in FIGS. 6 and 7 for monitoring the z alignment in operation together with graphical objects that monitor the x and y alignment. Similar relative positions are shown in FIG. 8(*a*) through 8(*e*) namely no eye being detected, and then the eye being much too far away, too far away, just right and too close respectively. The z alignment mechanism comprises concentric rings 600, 602, 604 which have varying colors in the same manner as described above with reference to FIG. 6. In addition, an x and y alignment monitoring system comprises a cross-hair object 606 and a spot 608. According to this embodiment, the crosshair represents an ideal position for the eye, with the centre point of the crosshair representing the centre point of the ideal pupil position. The spot 608 is then displayed on screen and represents the actual position of the eye as it moves. In this embodiment, the eye is aligned properly in the x and y plane for each of the different z positions illustrated.

The spot 608 is absent in the case of no eye being detected (FIG. 8(*a*)), and matches the color of the surrounding concentric rings in each of the other positions. According to this embodiment when the eye is in alignment in both the x and y plane and the z-axis, the entire set of secondary graphical objects, namely the spot 608 and the entire set of concentric rings 600, 602 and 604, will change to a particular color (being the "third color" mentioned above) which in a preferred embodiment is green. The operator of the instrument then knows that the eye is correctly aligned. According to this embodiment when the eye moves too close to the instrument the entire set of graphical objects 600, 602, 604 and 608 turn to a particular color, which may in an embodiment be red.

Figure 9:
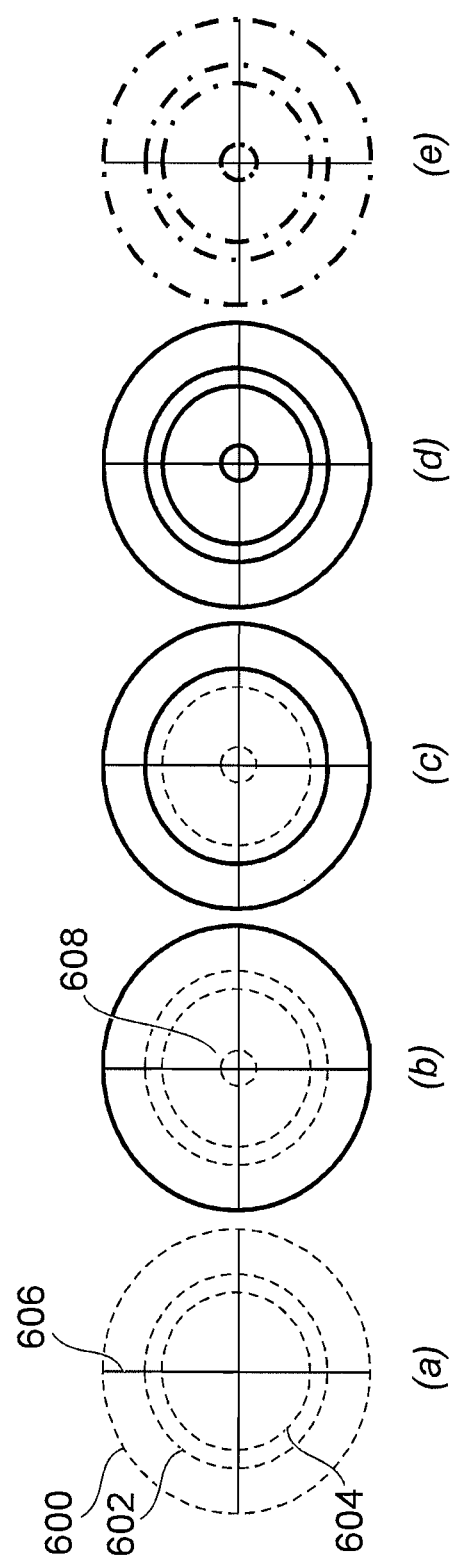
FIG. 9 illustrates aspects of the embodiment shown in FIG. 8.

FIG. 9 illustrates the graphical objects of FIG. 8 without the background eye image, for clarity of illustration. The same graphical objects 600, 602, 604, 606 and 608 are shown, and the positions shown in FIG. 9 (a) through 9 (e) correspond to the respective positions shown in FIG. 8 (a) through 8 (e).

The various features of this disclosure provide advantages with respect to the prior art. The graphical feedback is much more readily and intuitively understood by an operator of the equipment and can be very quickly translated into instructions for the patient or for manipulation of the instrument 100. It removes complexity from the operator's work and improves the speed and accuracy of the feedback given to the patient, with subsequent benefits relating to the quality of the image that is provided and the quality of diagnosis that can be made.

The first graphical object remains in a fixed position on the display, as it represents an ideal eye position. The second graphical object tracks the actual position of the eye. So, in use, the second graphical object moves with reference to the fixed reference point of the first graphical object. This relative motion of the two graphical objects is easy for a user of the instrument to track as it is easy to visually identify the objects and adjust their position.

The x and y alignment mechanism represents an improvement over existing x and y alignment mechanisms which provide a single graphical object and rely upon the alignment of two ellipses. By providing two customised graphical objects, a much more intuitive and easy to use system is provided. In particular, a combined crosshair and spot type arrangement is particularly intuitive and provides improved accuracy.

The z alignment mechanism represents an improvement over existing z alignment mechanisms, because the first, reference, graphical object is provided as a separate element from the second graphical object, which tracks and indicates the actual position of the eye, meaning that it can include markers representing a plurality of different positions and thus providing more information about the actual eye's z-position allowing for quicker and more accurate alignment adjustment by an operator.

It is possible for the first and second graphical objects to be overlaid upon the actual displayed image of the eye, in which case an operator would align the second graphical object with the centre of the pupil, as well as the first graphical object. However, in an alternative embodiment the actual image of the eye is not displayed on the screen. The alignment can be performed using the first and second graphical objects only as they represent an abstraction of the position of the eye with respect to the instrument. Not having the distracting background image of the eye makes this embodiment even easier to use, as the alignment is clearly marked against a chosen background, which may be a plain color.

Various improvements and modifications may be made to the above without departing from the scope of the invention. In particular the invention is not limited to any particular color or to any particular shape of graphical element. The disclosure may also be used to align two eyes simultaneously, rather than being limited to performing alignment of a single eye at a time. To achieve this, additional cameras may be provided as required. The processor may be common to the additional cameras, or distributed among them; and the images of the eyes and the graphical objects representing the alignment may be formed on different displays, or provided in different windows or frames on the same display.

We claim:

1. An alignment apparatus comprising:
   an ophthalmic or optometric instrument;
   a camera arranged to image a patient's eye, in use;
   a processor arranged to receive image data from the camera and to process the image data to determine an eye position by applying an edge detection algorithm to the image data and identifying the position of a limbal ring of an eye; and
   a display;
   wherein the processor is arranged to form on the display a first graphical object representative of an ideal eye position and a second graphical object representative of an actual eye position, as determined by the processor.

2. The apparatus of claim 1, comprising two cameras, each arranged to image a patient's eye.

3. The apparatus of claim 1, wherein the eye position is determined in three dimensions.

4. The apparatus of claim 1, wherein the processor is arranged to form on the display an image of a patient's eye, and the first and second graphical objects are overlaid upon the image.

5. The apparatus of claim 1, wherein the processor is arranged to form on the display a second graphical object having a first color in the event of a determined eye position being out of alignment with respect to an ideal eye position and to form on the display a second graphical object having a second color in the event of a determined eye position being in alignment with respect to an ideal eye position.

6. The apparatus of claim 1, wherein the first graphical object comprises a crosshair element.

7. The apparatus of claim 1, wherein the second graphical object comprises a spot, displayed at a center point of a pupil of an eye.

8. The apparatus of claim 1, wherein the first graphical object comprises a series of radially spaced markers.

9. The apparatus of claim 8, wherein one of the markers is graphically distinguished from the other markers and represents an ideal eye position.

10. The apparatus of claim 8, wherein the second graphical object comprises a marker at a radial position which is overlaid upon one of the radially spaced markers of the first graphical object or formed by changing a display property of one of the radially spaced markers of the first graphical object.

11. The apparatus of claim 8, wherein the first and second graphical objects comprise concentric ring shaped elements.

12. The apparatus of claim 1, wherein a history of an eye's motion can be represented by displaying two or more of the second graphical objects.

13. The apparatus of claim 1, wherein the first graphical object comprises a first crosshair graphical element and a second graphical element comprising a series of radially spaced markers.

14. The apparatus of claim 13, wherein the second graphical element comprises a first spot graphical element and a second graphical element comprising a marker at a radial position which is overlaid upon one of the radially spaced markers of the second graphical element of the first graphical object or formed by changing a display property of one of the radially spaced markers of the second graphical element of the first graphical object.

15. An alignment method comprising:
   positioning a patient's eye for examination by an ophthalmic or optometric instrument;
   imaging the eye with a camera;
   outputting image data from the camera to a processor;
   determining, at the processor, an eye position, by applying an edge detection algorithm to the image data and identifying a position of a limbal ring of the eye;

coupling a display with the processor; and forming on the display a first graphical object representative of an ideal eye position and a second graphical object representative of an actual eye position, as determined by the processor.

16. The method of claim 15, wherein an operator performs a visual inspection of the display, and adjusts the alignment of the patient's eye with respect to the instrument based on the visual inspection.

17. The method of claim 15, wherein the step of imaging the eye with a camera comprises imaging the eye with different first and second cameras.

18. The method of claim 15, wherein the eye position is determined in three dimensions.

19. The method of claim 15, wherein the processor forms on the display an image of a patient's eye, and overlays the first and second graphical objects upon the image of the eye.

20. The method of claim 15, wherein the processor forms on the display a second graphical object having a first color in the event of a determined eye position being out of alignment with respect to an ideal eye position and to form on the display a second graphical object having a second color in the event of a determined eye position being in alignment with respect to an ideal eye position.

21. The method of claim 15, wherein the first graphical object comprises a crosshair element.

22. The method of claim 15, wherein the second graphical object comprises a spot, displayed at a center point of a pupil of an eye.

23. The method of claim 15, wherein the first graphical object comprises a series of radially spaced markers.

24. The method of claim 23, wherein one of the markers is graphically distinguished from the other markers and represents an ideal eye position.

25. The method of claim 23, wherein the second graphical object comprises a marker at a radial position which is overlaid upon one of the radially spaced markers of the first graphical object or formed by changing a display property of one of the radially spaced markers of the first graphical object.

26. The method of claim 23, wherein the first and second graphical objects comprise concentric ring shaped elements.

27. The method of claim 15, wherein a history of the eye's motion is represented by displaying two or more of the second graphical objects.

28. The method of claim 15, wherein the first graphical object comprises a first crosshair graphical element and a second graphical element comprising a series of radially spaced markers.

29. The method of claim 28, wherein the second graphical element comprises a first spot graphical element and a second graphical element comprising a marker at a radial position which is overlaid upon one of the radially spaced markers of the second graphical element of the first graphical object or formed by changing a display property of one of the radially spaced markers of the second graphical element of the first graphical object.

30. A computer program product encoded with instructions that when run on a computer, cause the computer to receive image data; determine an eye position from the image data by applying an edge detection algorithm to the image data and identifying a position of a limbal ring of the eye; and transmit a display signal for forming on the display a first graphical object representative of an ideal eye position and a second graphical object representative of an actual determined eye position.

* * * * *